US010192641B2

(12) United States Patent
Vaske et al.

(10) Patent No.: US 10,192,641 B2
(45) Date of Patent: *Jan. 29, 2019

(54) METHOD OF GENERATING A DYNAMIC PATHWAY MAP

(75) Inventors: Charles J. Vaske, Santa Cruz, CA (US); Stephen C. Benz, Santa Cruz, CA (US); Joshua M. Stuart, Santa Cruz, CA (US); David Haussler, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/317,769

(22) Filed: Oct. 26, 2011

(65) Prior Publication Data
US 2012/0158391 A1 Jun. 21, 2012

Related U.S. Application Data

(63) Continuation-in-part of application No. 13/068,002, filed on Apr. 29, 2011.

(60) Provisional application No. 61/343,575, filed on Apr. 29, 2010.

(51) Int. Cl.
| | | |
|---|---|---|
| *G01N 33/48* | (2006.01) | |
| *G16H 50/30* | (2018.01) | |
| *G06F 19/12* | (2011.01) | |
| *G06F 17/30* | (2006.01) | |
| *G06F 19/20* | (2011.01) | |
| *G06F 19/24* | (2011.01) | |
| *G06F 19/00* | (2018.01) | |
| *G16H 50/20* | (2018.01) | |

(52) U.S. Cl.
CPC ....... *G16H 50/30* (2018.01); *G06F 17/30318* (2013.01); *G06F 19/12* (2013.01); *G06F 19/20* (2013.01); *G06F 19/24* (2013.01); *G06F 19/3456* (2013.01); *G06F 19/3475* (2013.01); *G06F 19/3481* (2013.01); *G16H 50/20* (2018.01); *Y02A 90/26* (2018.01)

(58) Field of Classification Search
None
See application file for complete search history.

(56) References Cited

U.S. PATENT DOCUMENTS

| 7,848,890 B2 | 12/2010 | Jung et al. |
| 8,515,680 B2 | 8/2013 | Pipke et al. |
| 8,635,029 B2 | 1/2014 | Gustafsson et al. |
| 2002/0004792 A1 | 1/2002 | Busa |
| 2003/0113761 A1 | 6/2003 | Tan et al. |
| 2004/0167763 A1 | 8/2004 | Liebman |
| 2006/0122792 A1 | 6/2006 | Jung et al. |
| 2007/0009530 A1 | 1/2007 | Altaba et al. |
| 2009/0186024 A1 | 7/2009 | Nevins et al. |
| 2010/0100331 A1 | 4/2010 | Gustafsson et al. |
| 2010/0130527 A1 | 5/2010 | Lehrer et al. |
| 2011/0093244 A1 | 4/2011 | Pipke et al. |

FOREIGN PATENT DOCUMENTS

| JP | 11500309 | 1/1999 |
| JP | 2006185412 | 1/2006 |
| JP | 2007011996 | 1/2007 |
| WO | 2005096207 | 10/2005 |
| WO | 2011001844 | 1/2011 |
| WO | WO 2011139345 | 11/2011 |

OTHER PUBLICATIONS

Alizadeh wt al., "Distinct types of diffuse large B-cell lymphoma identified by gene expression profiling," Nature Feb. 2000;403(6769):503-511.
Allison et al., "Microarray data analysis: from disarray to consolidation and consensus," Nat. Rev. Genet. Jan. 2006;7(1):55-65.
Ashbumer et al., Gene ontology: tool for the unification of biology. The Gene Ontology Consortium. Nat Genet May 2000;25(1):25-29.
Beer et al., "Predicting gene expression from sequence," Cell Apr. 2004;117(2):185-198.
Bengtsson et al., "Estimation and assessment of raw copy numbers at the single locus level," Bioinformatics (Oxford, England) 24, 759-767 (2008).
Bussey et al., "Integrating data on DNA copy number with gene expression levels and drug sensitivities in the NCI-60 cell line panel," Mol Cancer Ther 5, 853-867 (2006).
Cancer Genome Atlas Research Network. Comprehensive genomic characterization defines human glioblastoma genes and core pathways. Nature Oct. 2008;455(7216):1061-1068.
Chin et al., "Using array-comparative genomic hybridization to define molecular portraits of primary breast cancers," 26: 1959-1970 (2007).
de Visser et at., "Paradoxical roles of the immune system during cancer development," 6: 24-37 (2006).
Dudoit et al., "A prediction-based resampling method for estimating the number of clusters in a dataset," Genome Biol Jun. 2002;3(7):RESEARCH0036-RESEARCH0036.21.

(Continued)

*Primary Examiner* — Pablo S Whaley
(74) *Attorney, Agent, or Firm* — Kilpatrick Townsend & Stockton LLP

(57) ABSTRACT

A method of generating a dynamic pathway map (DPM) is provided. The method includes accessing a model database that stores a probabilistic pathway model that comprises a plurality of pathway elements, a first number of the plurality of pathway elements are cross-correlated and assigned an influence level for at least one pathway on the basis of known attributes, a second number of the plurality of pathway elements are cross-correlated and assigned an influence level for at least one pathway on the basis of assumed attributes. The method includes measuring a patient sample to identify measured attributes of the patient sample and using a plurality of the measured attributes of the patient sample, via an analysis engine, to modify the probabilistic pathway model to obtain the DPM, wherein the DPM has reference pathway activity information for a particular pathway, the reference pathway indicating deviations from the probabilistic pathway model.

9 Claims, 1 Drawing Sheet

(56) References Cited

OTHER PUBLICATIONS

Efroni et al., "Identification of key processes underlying cancer phenotypes using biologic pathway analysis," PLoS ONE 2007;2(5);e425.
Enerly et al., "miRNA-mRNA Integrated Analysis Reveals Roles for miRNAs in Primary Breast Tumors," 6: e16915, (2011).
Etemadmoghadam et al., "Integrated Genome-Wide DNA Copy Number and Expression Analysis Identifies Distinct Mechanisms of Primary Chemoresistance in Ovarian Carcinomas," Clinic.
Friedman et al., "Inferring cellular networks using probabilistic graphical models," Science Feb. 2004;303(5859):799-805.
Friedman et al., "Sequential Update of Bayesian Network Structure," Proceedings of the Thirteenth Conference on Uncertainty in Artificial Intelligence (UAI'97), Morgan Kaufman.
Gat-Viks et al., "A probabilistic methodology for integrating knowledge and experiments on biological networks," J. Comput. Biol. Mar. 2006;13(2):165-181.
Gat-Viks et al., "Refinement and expansion of signaling pathways: the osmotic response network in yeast," Genome Research Mar. 2007;17(3):358-367.
Gat-Viks et al., "The Factor Graph Network Model for Biological Systems," RECOMB'05 Proceedings of the 9th Annual international conference on Research in Computational Molecul.
Golub et al., "Molecular classification of cancer: class discovery and class prediction by gene expression monitoring," Science Oct. 1999;286(5439):531-537.
Gooch, J. L., Christy, B., and Yee, D., "STAT6 mediates interleukin-4 growth inhibition in human breast cancer cells," 4: 324-331 (2002).
Joshi-Tope et al., "Reactome: a knowledgebase of biological pathways," Nucleic Acids Res. Jan. 2005;33(Database issue):D428-32.
Kerr et al., "Analysis of variance for gene expression microarray data," J. Comput. Biol. 2000;7(6):819-837.
Konecny et al. Activity of the dual kinase Inhibitor lapatinib (GW572016) against HER-2-overexpressing and trastuzumab-treated breast cancer cells. Cancer Res 66, 1630-1639 (2.
Kuo et al., "A systems analysis of the chemosensitivity of breast cancer cells to the polyamine analogue PG-11047," BMC Med 7, 77, doi:1741-7015-7-77 [pII] 10.1186/1741-7015-7.
Lee et al., "Identifying regulatory mechanisms using individual variation reveals key role for chromatin modification," Proc. Natl. Acad. Sci. U.S.A. Sep. 2006;103(38)14062-14.
Miriam Ragle Aure et al., "A robust novel method for the integrated analysis of copy number and expression reveals new candidate driver genes in breast cancer," (2011).
Monks et al., "Feasibility of a high-flux anticancer drug screen using a diverse panel of cultured human tumor cell lines," J Natl Cancer Inst 83, 757-786 (1991).
Monti et al., "Consensus Clustering: A Resampling-Based Method for Class Discovery and Visualization of Gene Expression Microarray Data," Machine Learning 52, 91-118 (2003).
Muggerud et al., "Molecular diversity in ductal mom in situ (DCIS) and early invasive breast cancer," 4: 357-368) (2010).
Murphy et al., "Loopy belief propagation for approximate inference: An empirical study," Proceedings of Uncertainty in AI. 1999.
Naume et al., "Presence of bone marrow micrometastasis is associated with different recurrence risk within molecular subtypes of breast cancer," 1: 160-17, (2007).
Neve et al. A collection of breast cancer cell lines for the study of functionally distinct cancer subtypes. Cancer Cell 10, 515-527 (2006).
Ogata et al., KEGG: Kyoto Encyclopedia of Genes and Genomes, Nucleic Acids Res, Jan. 1999;27(1):29-34.).
Olshen et al., "Circular binary segmentation for the analysis of array-based DNA copy number data," Biostatistics (Oxford, England) 5, 557-572 (2004).
Paez et al. EGFR mutations in lung cancer: correlation with clinical response to gefitinib therapy. Science 304, 1497-1500 (2004).
Pagel et al., "The MIPS mammalian protein-protein interaction database," Bioinformatics Mar. 2005;21(6):832-834.
Parsons et al., "An Integrated Genomic Analysis of Human Glioblastoma Multiforme," Science Sep. 2008;321(5897):1807-1812.
Rranneberg et al. "Methylation profiling with a panel of cancer related genes: association with estrogen receptor," TP53 mutation status and expression subtypes in sporadic b.
Russnes et al., "Genomic architecture characterizes tumor progression paths and fate in breast cancer patients," Sci Transl Med Jun. 2010;2(38):38ra47).
Sachs et al., "Causal protein-signaling networks derived from multiparameter single-cell data," Science Apr. 2005;308(5721):523-529.
Scappini et al. Changes associated with the development of resistance to imatinib (STI571) in two leukemia cell lines expressing p210 Bcr/Abl protein. Cancer 100, 1459-1471 (2.
Segal et al., "From signatures to models: understanding cancer using microarrays," Nat Genet Jun. 2005;37 Suppl:S38-45.
Stephens et al., "Complex landscapes of somatic rearrangement in human breast cancer genomes," 462: 1005-1010) (2009).
Storey et al., "Statistical significance for genomewide studies," Proc. Natl. Acad. Sci. U.S.A. Aug. 2003;100(16):9440-9445.
Subramanian et al., "Gene set enrichment analysis: a knowledge-based approach for Interpreting genome-wide expression profiles," Proc. Natl. Acad. Sci. U.S.A. Oct. 2005; 102(4.
Tamayo et al.,-"Interpreting patterns of gene expression with self-organizing maps: methods and application to hematopoietic differentiation," Proc. Natl. Acad. Sci. U.S.A. 19.
Tarca et al., "A novel signaling pathway impact analysis," Bioinformatics Jan. 2009;25(1):75-82.
Troyanskaya et al., "Nonparametric methods for Identifying differentially expressed genes in microarray data," Bioinformatics Nov. 2002;18(11):1454-1461.
Tusher et al., "Significance analysis of microarrays applied to the ionizing radiation response," Proc. Natl. Acad. Sci. U.S.A. Apr. 2001;98(9):5116-5121.
Tusher at al., "V. G., Tibshirani, R. & Chu, G. Significance analysis of microarrays applied to the ionizing radiation response," Proc Natl Acad Sci U S A 98, 5116-5121, dol:1.
van de Vijver et al., "A Gene-Expression Signature as a Predictor of Survival in Breast Cancer," N Engl J Med Dec. 2002;347(25):1999-2009.
Loo et al., Allele-specific copy number analysis of tumors, 107: 16910-169154), 2010.
Weinstein et al., "Spotlight on molecular profiling: "Integromic" analysis of the NCI-60 cancer cell lines," Mol Cancer Ther 5, 2601-2605 (2006).
Wirapati et al., "Meta-analysis of gene expression profiles in breast cancer: toward a unified understanding of breast cancer subtyping and prognosis signatures," Breast Cance.
Schaefer et al., "PID: The Pathway Interaction Database," Nucleic Acids Res., 2009 (37):D674-679.
Kwoh et al. "Network analysis approach for biology," Cell. Mol. Life Sci., 2007 (64):1739-1751.
Cerami et al., "cPatch: open source software for collecting, storing, and querying biological pathways," Bioinformatics, 2006, 7(497):1-9.
Vaske, C. J., et al, "Inference of patient-specific pathway activities from multi-dimensional cancer genomics date using PARADIGM", Bioinformatics, 2010, i237-i245, 26(12).
European Patent Office, Extended European Search Report, EP11874850, completed Feb. 12, 2015.
U.S. Appl. No. 13/068,002, "Final Office Action", dated Apr. 14, 2016, 13 pages.
U.S. Appl. No. 13/068,002, "Final Office Action", dated Jun. 25, 2014, 13 pages.
U.S. Appl. No. 13/068,002, "Non-Final Office Action", dated Aug. 27, 2013, 17 pages.
U.S. Appl. No. 13/068,002, "Non-Final Office Action", dated Jul. 2, 2015, 18 pages.
U.S. Appl. No. 13/068,002, "Restriction Requirement", dated Nov. 23, 2012, 8 pages.
U.S. Appl. No. 14/577,522, "Non-Final Office Action", dated Jan. 26, 2018, 26 pages.

(56) References Cited

OTHER PUBLICATIONS

U.S. Appl. No. 14/577,522, "Restriction Requirement", dated Aug. 29, 2017, 6 pages.
U.S. Appl. No. 15/667,534, "Non-Final Office Action", dated May 17, 2018, 13 pages.
U.S. Appl. No. 15/667,534, "Restriction Requirement", dated Dec. 18, 2017, 7 pages.
U.S. Appl. No. 15/667,535, "Restriction Requirement", dated Feb. 21, 2018, 6 pages.
U.S. Appl. No. 15/667,544, "Non-Final Office Action", dated May 23, 2018, 14 pages.
U.S. Appl. No. 15/667,544, "Restriction Requirement", dated Dec. 18, 2017, 8 pages.
U.S. Appl. No. 15/667,535, "Non-Final Office Action", dated Jun. 14, 2018, 12 pages.
AU2017201919, "First Examination Report", dated Jul. 4, 2018, 4 pages.
CA2,796,272, "Office Action", dated Jul. 27, 2018, 6 pages.
CA3,007,805, "Office Action", dated Jul. 30, 2018, 5 pages.
CN201180032521, "First Office Action", dated Jan. 30, 2015, 5 pages.
CN201180032521, "Second Office Action", dated Oct. 30, 2015.
CN201180075918.7, "First Office Action", dated Mar. 1, 2016.
EP11777686, "Extended European Search Report", dated Feb. 11, 2016, 10 pages.
IL248380, "Office Action", dated May 22, 2018.
JP2017-000264, "Notice of Decision to Grant", dated Aug. 6, 2018, 3 pages.
JP2017-78768, "Notice of Decision to Grant", dated Jul. 30, 2018, 3 pages.
KR10-2012-7031376, "Notice of Decision to Grant", dated Jun. 25, 2018, 3 pages.
PCT/US2011/000752, "International Preliminary Report on Patentability", dated Oct. 30, 2012, 4 pages.
PCT/US2011/000752, "International Search Report and Written Opinion", dated Feb. 8, 2012, 6 pages.
PCT/US2011/001844, "International Preliminary Report on Patentability", dated Apr. 29, 2014, 4 pages.
KR10-2015-7010056, "Office Action", dated Aug. 23, 2018, 9 pages.
U.S. Appl. No. 13/068,002, "Non-Final Office Action", dated Sep. 21, 2018, 23 pages.
U.S. Appl. No. 14/577,522, "Final Office Action", dated Sep. 17, 2018, 23 pages.
CA3,007,713, "Office Action", dated Sep. 5, 2018, 6 pages.
EP11777686.4, "Office Action", dated Oct. 12, 2018, 5 pages.
KR10-2018-7027602, "Office Action", dated Nov. 2, 2018, 12 pages.

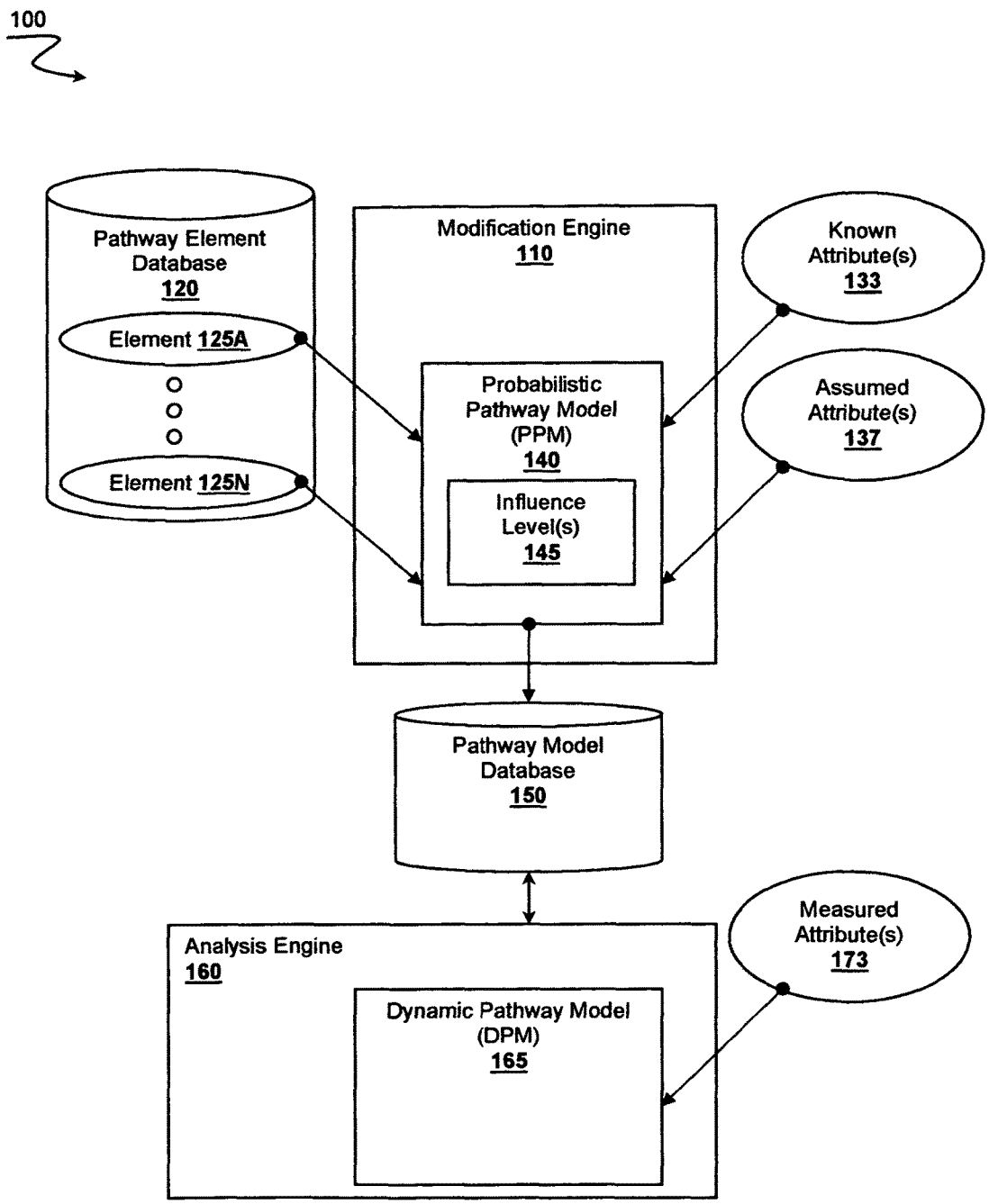

METHOD OF GENERATING A DYNAMIC PATHWAY MAP

RELATIONSHIP TO OTHER APPLICATIONS

This application is a continuation-in-part application of US Non-provisional patent application Ser. No. 13/068,002, entitled "PATHWAY RECOGNITION ALGORITHM USING DATA INTEGRATION ON GENOMIC MODELS (PARADIGM)" filed 29 April, 2011, which is incorporated by reference herein, and which is related to and claims priority from U.S. Provisional Patent Application Ser. No. 61/343,575 entitled "PATHWAY RECOGNITION ALGORITHM USING DATA INTEGRATION ON GENOMIC MODELS (PARADIGM)" filed 29 Apr. 2010, which is herein incorporated by reference in its entirety.

This invention was made partly using funds from the following United Stated Federal agencies: NSF CAREER award 0845783, National Cancer Institute Contract/Grant numbers 5R21CA135937-02 and 1U24CA143858-01, and National Institute of Health Training Grant number T32 GM070386-01. The US Federal Government has certain rights to this invention.

FIELD OF THE INVENTION

The field of the invention is computational biology, especially as it relates to analysis of pathways and pathways elements to provide dynamic pathway maps.

BACKGROUND

In the past decade, few computational approaches were available for incorporating pathway knowledge to interpret high-throughput datasets, and more recently, certain approaches have been proposed that incorporate pathway topology. For example, signaling pathway impact analysis (SPIA) uses a method analogous to Google's PageRank to determine the influence of a gene in a pathway. Consequently, more influence is placed on genes that link out to many other genes. SPIA was successfully applied to different cancer datasets (lung adenocarcinoma and breast cancer) and shown to outperform overrepresentation analysis and gene set enrichment analysis for identifying pathways known to be involved in these cancers. However, while SPIA provided significant advantages in interpreting cancer datasets using pathway topology, SPIA is generally limited to using only a single type of genome-wide data. Consequently, as information for gene copy number, DNA methylation, somatic mutations, mRNA expression, and microRNA expression are not integrated into SPIA, analytic and predictive value of SPIA remains highly restricted, particularly where a more global analysis is required.

Still further, all or almost all of the currently known pathway analyses fail to incorporate interdependencies among genes in a pathway that can increase the detection signal for pathway relevance. Additionally, most known models treat all gene alterations as equal, a premise that is likely no representative for most biological systems. Further complicating the issue is the fact that many functional nucleic acids (for example, microRNAs) are pleiotropic, acting in several pathways with different roles.

Therefore, even tough numerous systems and methods of pathway analysis known in the art, all or all of them suffer from one or more disadvantage. Consequently, there is still a need for improved systems and methods of pathway analysis.

SUMMARY OF THE INVENTION

The inventors have discovered various systems and methods of pathway analysis that allow for integration of multiple attributes of multiple pathway elements (typically of one or more pathways) where at least one pathway element has an a priori known attribute, where at least another pathway element has an assumed attribute, where the pathway elements are cross-correlated and assigned specific influence levels on at least one pathway to so construct a probabilistic pathway model (PPM). Measured attributes for multiple elements of a patient sample are then used in conjunction with the PPM to so produce a patient sample specific dynamic pathway map (DPM).

In one aspect of the inventive subject matter, the inventors contemplate a method of generating a dynamic pathway map (DPM) in which in one step access is provided to a pathway element database that stores a plurality of pathway elements, wherein each pathway element is characterized by its involvement in at least one pathway. In another step, access is provided to a modification engine that is coupled to the pathway element database, and the modification engine is used to associate a first pathway element with at least one a priori known attribute. In yet another step, the modification engine is used to associate a second pathway element with at least one assumed attribute, and in yet a further step, the modification engine is used to cross-correlate and assign an influence level of the first and second pathway elements for at least one pathway using the known and assumed attributes, respectively, to thereby form a probabilistic pathway model. Finally, the probabilistic pathway model is used, via an analysis engine, to derive from a plurality of measured attributes for a plurality of elements of a patient sample the DPM having reference pathway activity information for a particular pathway.

Most preferably, the pathway is within a regulatory pathway network, and particularly contemplated regulatory pathway networks include an ageing pathway network, an apoptosis pathway network, a homeostasis pathway network, a metabolic pathway network, a replication pathway network, and an immune response pathway network. Likewise, the pathway may also be within a signaling pathway network and/or within a network of distinct pathway networks. For example, suitable signaling pathway networks include calcium/calmodulin dependent signaling pathway network, a cytokine mediated signaling pathway network, a chemokine mediated signaling pathway network, a growth factor signaling pathway network, a hormone signaling pathway network, a MAP kinase signaling pathway network, a phosphatase mediated signaling pathway network, a Ras superfamily mediated signaling pathway network, and a transcription factor mediated signaling pathway network.

In further especially contemplated aspects, preferred pathway elements are proteins. For example, preferred proteins include a receptor, a hormone binding protein, a kinase, a transcription factor, a methylase, a histone acetylase, and a histone deacetylase. Where preferred pathway elements are nucleic acids, such nucleic acids will typically include a protein coding sequence, a genomic regulatory sequence, a regulatory RNA, and a trans-activating sequence.

Most typically, the reference pathway activity information is specific with respect to a normal tissue, a diseased tissue, an ageing tissue, and/or a recovering tissue. Known and assumed attributes are typically and independently a compound attribute, a class attribute, a gene copy number, a transcription level, a translation level, or a protein activity, while the measured attributes are preferably a mutation, a differential genetic sequence object, a gene copy number, a transcription level, a translation level, a protein activity, and/or a protein interaction.

Therefore, in another aspect of the inventive subject matter, the inventors contemplate a method of generating a dynamic pathway map (DPM) in which in one step access to a model database is provided that stores a probabilistic pathway model that comprises a plurality of pathway elements. As noted before, it is generally preferred that a first number of the plurality of pathway elements are cross-correlated and assigned an influence level for at least one pathway on the basis of known attributes, and that a second number of the plurality of pathway elements are cross-correlated and assigned an influence level for at least one pathway on the basis of assumed attributes. In a further step, a plurality of measured attributes for a plurality of elements of a patient sample is used, via an analysis engine, to modify the probabilistic pathway model to so obtain the DPM, wherein the DPM has reference pathway activity information for a particular pathway.

In such methods, it is generally preferred that the pathway is within a regulatory pathway network, a signaling pathway network, and/or a network of distinct pathway networks, and/or that the pathway element is a protein (e.g., a receptor, a hormone binding protein, a kinase, a transcription factor, a methylase, a histone acetylase, a histone deacetylase, etc.) or a nucleic acid (e.g., a genomic regulatory sequence, regulatory RNA, trans-activating sequence, etc.). With respect to the reference pathway activity information, the known attribute, the assumed attribute, and the measured attribute, the same considerations as outlined above apply.

Therefore, and viewed from a different perspective, a method of analyzing biologically relevant information may include a step of providing access to a model database that stores a dynamic pathway map (DPM), wherein the DPM is generated by modification of a probabilistic pathway model with a plurality of measured attributes for a plurality of elements of a first cell or patient sample. In another step, a plurality of measured attributes for a plurality of elements of a second cell or patient sample is obtained, and the DPM and the plurality of measured attributes for the plurality of elements of the second cell or patient sample are used, via an analysis engine, to determine a predicted pathway activity information for the second cell or patient sample.

In especially preferred aspects of such methods the measured attributes for the plurality of elements of the first cell or patient sample are characteristic for a healthy cell or tissue, a specific age of a cell or tissue, a specific disease of a cell or tissue, a specific disease stage of a diseased cell or tissue, a specific gender, a specific ethnic group, a specific occupational group, and/or a specific species. Moreover, it should be noted that the measured attributes for the plurality of elements of the second cell or patient sample will include information about a mutation, a differential genetic sequence object, a gene copy number, a transcription level, a translation level, a protein activity, and/or a protein interaction.

Most typically, the first and second samples are obtained from the same cell or patient, and it should be appreciated that treatment (e.g., radiation, administration of a pharmaceutical) may be provided to the cell or patient before obtaining the plurality of measured attributes for the plurality of elements of the second cell or patient sample. Where contemplated methods are used in the context of drug discovery, it is noted that the treatment includes administration of a candidate molecule to the cell (e.g., where the candidate molecule is a member of a library of candidate molecule).

In especially preferred aspects, the predicted pathway activity information identifies an element as a hierarchical-dominant element in at least one pathway, and/or identifies the element as a disease-determinant element in at least one pathway with respect to a disease. To facilitate presentation, a graphical representation of predicted pathway activity information may be provided, and/or a treatment recommendation may be generated that is at least in part based on the predicted pathway activity information. Of course, it should be appreciated that the predicted pathway activity information may be used to formulate a diagnosis, a prognosis for a disease, or a recommendation selected from the group consisting of a selection of a treatment option, and/or a dietary guidance, or to identify an epigenetic factor, a stress adaptation, a state of an organism, and/or a state of repair or healing.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1 is a schematic of an exemplary computer system to produce a dynamic pathway map according to the inventive subject matter.

DETAILED DESCRIPTION

The inventors have developed systems and methods where multiple attributes of multiple pathway elements are integrated into a probabilistic pathway model that is then modified using patient data to produce a dynamic pathway map. Most significantly, it should be appreciated that the attributes for pathway elements within a pathway need not be known a priori. Indeed, at least some of the attributes of at least some pathway elements are assumed. The pathway elements are then cross-correlated and assigned specific influence levels on or more pathways to so construct the probabilistic pathway model, which is preferably representative of a particular reference state (e.g., healthy or diseased). Measured attributes for multiple elements of a patient sample are then used in conjunction with the probabilistic pathway model to so produce a patient sample specific dynamic pathway map that provides reference pathway activity information for one or more particular pathways.

It should be particularly appreciated that integration of multiple types of attributes for one or more pathway elements in conjunction with (reasonably) assumed multiple types of attributes for one or more other pathway elements will allow for a significantly less restricted analysis and with that allows for multi-factorial analysis having a high degree of accuracy and resolution. Indeed, it should be noted that contemplated systems and methods allow production of detailed and textured results on the basis of relatively few measured patient sample attributes. Of course, it should also be noted that contemplated systems and methods will allow input of more than one kind of attributes for one or more pathway elements to generate an output of more than one kind of attributes for one or more pathway elements, where input and output attributes and pathway elements may be entirely distinct. For example, and viewed from a different perspective, patient-specific genomic inferences on the state of gene activities, complexes, and cellular processes may be drawn on the basis of a predetermined probabilistic pathway model.

It should be noted that while the following description is drawn to a computer/server based pathway analysis system, various alternative configurations are also deemed suitable and may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Moreover, the following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the current document "coupled with" should also be construed to mean "communicatively coupled with". For example, Overview In FIG. 1 an exemplary overview of pathway analysis ecosystem 100 is presented. Ecosystem 100 can include pathway element database 120 preferably storing a plurality of pathway elements 125A through 125N, collectively referred to as pathway elements 125. Each of pathway elements 125 can be characterized by its involvement with one or more pathways. Elements 125 can be considered separately manageable data objects comprising one or more properties or values describing the characteristics of the element. In some embodiments, elements 125 can be considered an n-tuple of properties or values, where each property member of an element 125 tuple can be compared, analyzed, contrasted, or otherwise evaluated against other property members in other element tuples.

Modification engine 110 communicatively couples with pathway element database 120, possibly over a network link (e.g., LAN, WAN, Internet, VPN, etc.). In some embodiments, pathway element database 120 could be local to modification engine 110, while in other embodiments, pathway element database 120 could be remote from modification engine 110. For example, pathway element database 120 could be accessed via the National Lambda Rail (see National Lambda rail website) or the Internet. Further, modification engine 110, or ecosystem 100 for that matter, can be accessed by users over the network, possibly in exchange for a fee.

Modification engine 110 obtains one or more of elements 125 from pathway element database 120 for analysis. Preferably, modification engine 110 associates at least one of elements 125 (e.g., elements 125A) with at least one a priori known attribute 133. Further, modification 110 also associates another element, element 125N for example, with assumed attribute 137. In some embodiments, modification engine 110 can make the associations automatically based on inference rules, programmatic instructions, or other techniques. For example, known attributes 137 could be obtained from known research while assumed attributes 137 could be mapped out according to an attribute parameterized space where modification engine 110 serially, or in parallel, walks through the assumed attribute space. In other embodiments, a user can manually associate attributes 133 or 137 as desired through one or more user interfaces (not shown), possibly operating through an HTTP server or other suitable interfacing technology.

Modification engine 110 further cross-correlates pathway elements 125 for one or more pathways using known attributes 133 and assumed attributes 137. Further, modification engine 110 assigns one or more influence levels 145 to elements 125. Through cross-correlation and assignment of influence levels 145, modification engine 110 constructs probabilistic pathway model 140 outlining how pathways might be influenced by assumed attributes 137 or other factors.

In some embodiments, probabilistic pathway model 140 can be stored within pathway model database 150 for archival purposes, or for analysis as indicated. As with elements 125, probabilistic pathway model 140 can also be stored as a distinct manageable data object having properties or values describing the characteristics of the model, possibly as an n-tuple. Models 145, or even elements 125, can be stored according to any desirable schema. Example suitable database that can be used to construct element database 120 or model database 140 include MySQL, PostgreSQL, Oracle, or other suitable databases. In some embodiments, the data objects (e.g., elements 125, probabilistic pathway model 145, etc.) can be multiply indexed via their properties or values in a manner allowing easy searching or retrieval.

Ecosystem 100 preferably includes analysis engine 160 configured to further analyze probabilistic pathway model 150 with respect to actual data. In the example shown, analysis engine 160 obtains probabilistic pathway model 150, possibly under direction of a user or researcher, to derive dynamic pathway model 165. Preferably, dynamic pathway model 160 is derived by comparing one or more measured attributes 173 from a patient sample with the attributes associated with probabilistic pathway model 140. Thus, analysis engine 160 seeks to modify, update, correct, or otherwise validate probabilistic pathway model 140 to form dynamic pathway model 165. Once complete, dynamic pathway model 165 can be stored within a model database. In more preferred embodiments, analysis engine 160 can configure one or more output devices (e.g., a display, a printer, a web server, etc.) to present dynamic pathway model 165.

Analysis

Using a system according to the inventive subject matter will therefore typically include a pathway element database. As already noted above, it should be appreciated that the database may be physically located on a single computer, however, distributed databases are also deemed suitable for use herein. Moreover, it should also be appreciated that the particular format of the database is not limiting to the inventive subject matter so long as such database is capable of storing and retrieval of multiple pathway elements, and so long as each pathway element can be characterized by its involvement in at least one pathway.

With respect to contemplated pathway elements, it should be noted that all elements that are part of a pathway are included herein. Consequently, suitable pathway elements will include one or more proteins (which may or may not be modified, e.g., via glycosylation, myristoylation, etc.), alone or in complex with other cellular components, various nucleic acids (genomic DNA, extrachromosomal DNA, hnRNA, siRNA, mRNA, rRNA, etc) which may be a native nucleic acid or a recombinant nucleic acid, lipids, hormones, second messengers, and pharmaceutically active agents provided as therapeutic or preventive agent. Thus, and viewed from a different perspective, contemplated pathway elements may have a variety of functions, and especially preferred functions include various enzymatic functions. For example, suitable functions are kinases/phosphatases, polymerases/hydrolases, proteases, hydrolases (and especially GTPase), hydroxylases, methyl transferases/methylases, etc.

Therefore, where a pathway element is a protein, suitable pathway elements include various receptors, hormone binding proteins, kinases, transcription factors, initiation factors, methylases and methyl transferases, histone acetylases, and histone deacetylases. Similarly, where the pathway element is a nucleic acid, contemplated pathway elements will include those that encode a protein sequence, one or more genomic regulatory sequences, regulatory RNA, and a transactivating sequences.

Depending on the particular pathway element, it should therefore be appreciated that the nature of the pathway may vary considerably, and all known pathways are deemed suitable for use herein. For example, contemplated pathways may be involved in signal transduction, in cell cycling, in cell growth and/or metabolism, in repair mechanisms (and especially in DNA repair), and in neural signaling. Consequently, especially preferred pathways include calcium/calmodulin dependent signaling pathways and functionally associated pathway networks, a cytokine mediated signaling pathway and functionally associated pathway networks, a chemokine mediated signaling pathway and functionally associated pathway networks, a growth factor signaling pathway and functionally associated pathway networks, a hormone signaling pathway and functionally associated pathway networks, a MAP kinase signaling pathway and functionally associated pathway networks, a phosphatase mediated signaling pathway and functionally associated pathway networks, a Ras superfamily mediated signaling pathway and functionally associated pathway networks, and a transcription factor mediated signaling pathway and functionally associated pathway networks. Therefore, it should be appreciated that the pathways may be individual pathways as well as pathways within a pathway network, and even within a network of distinct pathway networks. For example, the pathways contemplated herein may be within a regulatory pathway network. For example, contemplated pathway networks include an ageing pathway network, an apoptosis pathway network, a homeostasis pathway network, a metabolic pathway network, a replication pathway network, and an immune response pathway network.

Thus, it should be readily apparent that the type and numerical value of the attribute of the pathway element may vary considerably, and that the particular pathway element will in large part determine the type and numerical value of the attribute. For example, where the pathway element is a nucleic acid, the attribute may be a copy number, a particular haplotype or mutation, strength of a regulatory element (e.g., promoter, repressor, etc.), transcription level or translation level. Moreover, contemplated attributes will also include class attributes (e.g., gene is activatable by particular transcription factor, or sensitive to particular hormone response element, etc.) or may be a compound attribute (e.g., representative of at least two different attributes). Similarly, where the pathway element is a protein, the attribute may be quantity of translation, protein activity, requirement for a cofactor, requirement for formation of a multi-protein complex to provide activity, etc.).

As will be readily apparent from the above, at least some of the attributes for at least some of the pathway elements will be known from prior study and publication and can therefore be used in contemplated systems and methods as a priori known attributes for the specific pathway element. On the other hand, it should be appreciated that numerous attributes are not known a priori, however, that a large variety of such unknown attributes can be assumed with a reasonably good expectation of accuracy. For example, where the pathway element is a genomic sequence for a receptor, and where that sequence is preceded by a trans-activator binding sequence element, it can be reasonably assumed that one attribute of the pathway element is a requirement for binding of a trans activator. Moreover, where the strength of trans-activation is known for similarly controlled sequences, the transcription level of the pathway element can be reasonably inferred.

Thus, it should be noted that the assumed attributes are not arbitrarily assumed values, but that the assumption is based on at least partially known information. Moreover, it should be noted that the kind and value of the assumed attribute is also a function of a reference pathway. For example, and most typically, the reference pathway is a pathway of a healthy cell. Thus, the numerical range and kind of attribute will typically be reflective of that of a normal cell. However, it should be recognized that non-normal cells may also be used to establish a reference pathways.

It should be particularly recognized that since the attribute of a pathway element is often dependent on one or more attributes of at least one or more other pathway elements, multi-dimensional pathway maps can now be constructed in a conceptually simple and effective manner without the need for quantitative coverage of each attribute. Indeed, by virtue of having the attributes not only express numerical linear values but also functional information and interdependencies, complex pathway patterns can now be established with remarkable resolution and accuracy.

Such pathway patterns are typically produced using a modification engine that is coupled to the pathway element database, wherein the modification engine is used (1) to associate a first pathway element with at least one a priori known attribute, (2) to associate a second pathway element with at least one assumed attribute, and (3) to cross-correlate and assign an influence level of the first and second pathway elements for at least one pathway using the known and assumed attributes, respectively, to ultimately form a probabilistic pathway model. For example, association of the first pathway element with at least one a priori known attribute can be done in numerous manners. However, it is particularly preferred that the attribute is expressed as one of an n-tuple of attributes that is directly associated with the pathway element. Most typically, the known attribute is derived from a peer-reviewed publication. However, secondary information sources (e.g., compiled and publicly available information from various databases such as SWISSPROT, EMBL, OMIM, NCI-PID, Reactome, Biocarta, KEGG, etc.) are also deemed suitable. Similarly, assumed attributes can be manually associated with the pathway element, and more preferably in an at least semi-automated manner.

Cross-correlation can be achieved through numerous techniques. In some embodiments, pathway elements can be cross-correlated manually. However, in more preferred embodiments elements can be cross-correlated through one or more automated techniques. For example, numerous elements can be analyzed with respect to their properties via a modification engine that seeks to find possible correlation. The modification engine can be configured to seek such correlations via multi-variate analysis, genetic algorithms, inference reasoning, or other techniques. Examples of inference reason could include application of various forms of logic including deductive logic, abductive logic, inductive logic, or other forms of logic. Through application of different forms of logic, especially abductive or inductive logic, contemplated engines are capable of discovering possible correlations that a researcher might otherwise overlook. Another example of inference reasoning can include applications using inference on probabilistic models such as belief propagation, loopy belief propagation, junction trees, variable elimination or other inference methods.

Influence levels represent a quantitative value that an assumed attribute has on a pathway comprising elements with known attributes. Influence levels can comprise single values or multiple values. Example of a single value could include a weighting factor, possibly as an absolute value or a normalized value relative to other known influences within the pathway system under evaluation. Example multi-valued influence levels can include a range of values with a possible distribution width. Further, initial values of an influence level can be established through various techniques including being manually set. In more preferred embodiments, the initial value can be established through a manual estimation formulated by the modification engine. For example, the relative "distance" according to one or more element or pathway properties can be used to weight an influence level. In another example, the influence levels can be determined by maximizing the likelihood of the influence levels between all of the other values within the pathway system.

Cross-correlation and assignment of influence is then established based on the obtained and assumed attributes for the pathway elements. Moreover, as the pathway elements are already known pathway elements, it should be noted that the association of the elements to the respective pathways is a priori established. However, and in contrast to heretofore known systems and methods, the so established probabilistic pathway model allows for prediction of functional interrelations and weighted effects for each element within a given pathway using the cross-correlation and assignment of influence. Of course, it should be appreciated that the probabilistic pathway model can be established for healthy cells and tissue as well as for aged, challenged, or otherwise diseased cells or tissue.

Most preferably, an analysis engine will then employ the probabilistic pathway model to derive a dynamic pathway map from a plurality of measured attributes for a plurality of elements of a patient sample. For example, a patient sample may be derived from a biological fluid, a biopsy, or surgical specimen, and will typically analyzed using methods well known in the art. Therefore, and among other suitable attributes, measured attributes will include mutations, differential genetic sequence object, gene copy number for one or more particular gene, transcription level for one or more particular gene, translation level for one or more particular protein, protein activity, protein interaction, presence and/or quantity of an analyte (e.g., metabolite) or marker of a disease, etc.

In particularly preferred aspects, the measured attributes are fed into the probabilistic pathway model to so arrive at a dynamic pathway map that can indicate deviations from the probabilistic pathway model. Thus, it should be appreciated that the dynamic pathway map will provide a user with reference pathway activity information for a particular pathway (which can be specific with respect to a normal tissue, a diseased tissue, an ageing tissue, or a recovering tissue, etc.). Consequently, and viewed form a different perspective, the dynamic pathway map will allow a user to readily identify information related to one or more pathways in a patient sample based on a relatively limited number of measured attributes.

Therefore, the inventors also contemplate a method of generating a dynamic pathway map in which a user is provided access to a model database that stores a probabilistic pathway model that comprises a plurality of pathway elements. Of course, such access may be controlled in a variety of manners as the particular access protocol will be at least in part determined on the particular use. However, it is generally preferred that the access is a pay-per-use access or a pre-authorized access. Alternatively, the model database may also be accessible via a publicly accessible network. As already discussed above, it is generally preferred that at least some of the plurality of pathway elements are cross-correlated and assigned an influence level for at least one pathway on the basis of known attributes, and that another number of the plurality of pathway elements are cross-correlated and assigned an influence level for at least one pathway on the basis of assumed attributes, and that an analysis engine modifies the probabilistic pathway model with a plurality of measured attributes for a plurality of elements of a patient sample to obtain the dynamic pathway map, wherein the dynamic pathway map includes most preferably reference pathway activity information for a particular pathway.

Of course, it should be appreciated that contemplated systems and methods are not only suitable for analysis of a first sample relative to a standard pathway model (e.g., representing healthy donor), but that such systems and methods also allow intra-patient analysis of diseased tissue vis-à-vis healthy tissue to so predict a pathway activity information for a tissue. Therefore, using two samples from the same patient (i.e., from diseased tissue and non-diseased tissue), susceptibility of a diseased tissue to certain pharmaceuticals can be predicted. Consequently, the inventors also contemplate a method of analyzing biologically relevant information in which access to a model database is provided that stores a dynamic pathway map, wherein the DPM is generated by modification of a probabilistic pathway model with a plurality of measured attributes for a plurality of elements of a first cell or patient sample. Subsequently, a plurality of measured attributes are obtained for a plurality of elements of a second cell or patient sample, and the dynamic pathway map and the plurality of measured attributes for the plurality of elements of the second cell or patient sample are then used by an analysis engine to determine a predicted pathway activity information for the second cell or patient sample.

Consequently, the measured attributes for the plurality of elements of the first cell or patient sample may be characteristic for a healthy cell or tissue, a specific age of a cell or tissue, a specific disease of a cell or tissue, a specific disease stage of a diseased cell or tissue, a specific gender, a specific ethnic group, a specific occupational group, and even a specific species. So computed information may provide valuable information about actual or likely pathway differences with respect to occupation, pharmaceutical treatment, predisposition to a disease, etc. Thus, first and second samples may obtained from the same cell or patient concurrently, or at different times (most typically after treatment has commenced). While numerous uses of systems and methods presented herein are contemplated, particularly preferred uses include those in which a patient is tested for susceptibility of a diseases cell toward one or more drugs based on the DPM, and drug discovery. In such uses, a patient or patient sample may be subjected to a treatment (typically surgery, radiation, and administration of a pharmaceutical), and then receive a second pharmaceutical of potential therapeutic value.

Using such systems and methods, it should be recognized that the predicted pathway activity information may be able to identify a pathway element as a hierarchical-dominant element in at least one pathway, and/or as a disease-determinant element in at least one pathway with respect to a disease. Consequently, pharmaceutical intervention can be used in a targeted fashion with high chances of achieving the desired outcome. Where the predicted pathway activity information is provided to a physician, it is generally preferred to generate a graphical representation of predicted pathway activity information to render the information more relevant to the needs of a practitioner. Moreover, it is contemplated that the predicted pathway activity information may be used by the system and/or user to formulate a diagnosis, a prognosis for a disease, or a recommendation (e.g., selection of a treatment option or dietary guidance). Alternatively, or additionally, the predicted pathway activity information can also be used to identify an epigenetic factor, a stress adaptation, a state of an organism, and/or a state of repair or healing.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A processor-based method of generating a dynamic pathway map (DPM), comprising:
   accessing a model database that stores a probabilistic pathway model that comprises a plurality of pathway elements;
   assigning an influence level for at least one pathway of a first number of the plurality of pathway elements on the basis of known attributes;
   cross correlating the first number of the plurality of pathway elements;
   assigning an influence level for at least one pathway on the basis of assumed attributes;
   measuring a patient sample to identify measured attributes of the patient sample, based on a genome-scale assay;
   modifying the probabilistic pathway model by using a plurality of the measured attributes for a plurality of elements of the patient sample, via an analysis engine, the modifying comprising:
      obtaining a factor graph representing states of entities in a cell and interactions between the entities, wherein the factor graph encodes a state of the cell using a random variable for each entity and wherein the factor graph has reference pathway activity information for a particular pathway, the reference pathway indicating deviations from the probabilistic pathway model; and
   formulating a treatment option for the patient based on the reference pathway activity of the factor graph, wherein at least one of the above method operations is performed through a processor.

2. The method of claim 1 wherein the pathway is within a regulatory pathway network, a signaling pathway network, or a network of distinct pathway networks.

3. The method of claim 1 wherein the pathway element is a protein selected from the group consisting of a receptor, a hormone binding protein, a kinase, a transcription factor, a methylase, a histone acetylase, and a histone deacetylase or a nucleic acid is selected from the group consisting of a genomic regulatory sequence, a regulatory RNA, and a trans-activating sequence.

4. The method of claim 1 wherein the reference pathway activity information is specific with respect to a normal tissue, a diseased tissue, an ageing tissue, or a recovering tissue.

5. The method of claim 1 wherein the known attribute is selected from the group consisting of a compound attribute, a class attribute, a gene copy number, a transcription level, a translation level, and a protein activity.

6. The method of claim 1 wherein the assumed attribute is selected from the group consisting of a compound attribute, a class attribute, a gene copy number, a transcription level, a translation level, and a protein activity.

7. The method of claim 1 wherein the measured attributes are selected from the group consisting of a mutation, a differential genetic sequence object, a gene copy number, a transcription level, a translation level, a protein activity, and a protein interaction.

8. The method of claim 1, wherein modifying the probabilistic pathway model comprises:
   converting the probabilistic pathway into a directed graph with each edge of the directed graph labeled with one of a positive or a negative influence.

9. The method of claim 8 further comprising:
   converting each of the interactions to a single edge of the directed graph.

* * * * *